(12) United States Patent
Rosser

(10) Patent No.: US 10,701,974 B2
(45) Date of Patent: Jul. 7, 2020

(54) ELECTRONIC SMOKING DEVICE AND ATOMIZER

(71) Applicant: Fontem Holdings 2 B.V., Amsterdam (NL)

(72) Inventor: Chris Rosser, Cambridge (GB)

(73) Assignee: Fontem Holdings 2 B.V., Amsterdam (NL)

( * ) Notice: Subject to any disclaimer, the term of this patent is extended or adjusted under 35 U.S.C. 154(b) by 166 days.

(21) Appl. No.: 15/739,613

(22) PCT Filed: Jun. 24, 2016

(86) PCT No.: PCT/EP2016/064678
§ 371 (c)(1),
(2) Date: Dec. 22, 2017

(87) PCT Pub. No.: WO2016/207357
PCT Pub. Date: Dec. 29, 2016

(65) Prior Publication Data
US 2018/0177236 A1    Jun. 28, 2018

(30) Foreign Application Priority Data
Jun. 25, 2015    (EP) .................................... 15173933

(51) Int. Cl.
*A24F 13/00*    (2006.01)
*A24F 17/00*    (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ........ A24F 47/008; A24F 47/002; H05B 3/44
(Continued)

(56) References Cited

U.S. PATENT DOCUMENTS

2012/0234821 A1    9/2012  Shimizu
2013/0192615 A1*   8/2013  Tucker .................... H05B 3/12
                                                       131/328
(Continued)

FOREIGN PATENT DOCUMENTS

CN    202068933 U    12/2011
CN    202873795 U    4/2013
(Continued)

*Primary Examiner* — Hae Moon Hyeon
(74) *Attorney, Agent, or Firm* — Dykema Gossett PLLC

(57) ABSTRACT

The invention relates to an atomizer for an electronic smoking device, to a cartomizer with an atomizer and to an electronic smoking device with an atomizer. In order to improve atomizing efficiency, the atomizer comprises a heating coil made of a heating wire with a first section and a second section, wherein the first section comprises an electrical resistance per length unit that differs from an electrical resistance per length unit of the second section, and wherein the heating coil has a first winding, a last winding and at least one inner winding between the first winding and the last winding, wherein the at least one inner winding comprises the first section, the first winding comprises the second section, and the last winding ROM comprises a third section, wherein the electrical resistance per length unit of the third section corresponds to the electrical resistance per length unit of the second section.

20 Claims, 4 Drawing Sheets

(51) Int. Cl.
*A24F 25/00* (2006.01)
*A24F 47/00* (2020.01)
*A61M 11/04* (2006.01)
*A61M 15/06* (2006.01)
*H05B 3/44* (2006.01)
*A61M 16/00* (2006.01)
*A61M 15/00* (2006.01)

(52) U.S. Cl.
CPC .......... *H05B 3/44* (2013.01); *A61M 15/0025* (2014.02); *A61M 2016/0024* (2013.01); *A61M 2016/0039* (2013.01); *A61M 2205/3653* (2013.01); *A61M 2205/8206* (2013.01); *H05B 2203/021* (2013.01)

(58) Field of Classification Search
USPC .................................................. 131/329, 328
See application file for complete search history.

(56) References Cited

U.S. PATENT DOCUMENTS

| | | | | |
|---|---|---|---|---|
| 2013/0192623 | A1* | 8/2013 | Tucker | H05B 3/026 131/329 |
| 2013/0213419 | A1* | 8/2013 | Tucker | A24F 47/008 131/328 |
| 2014/0224244 | A1* | 8/2014 | Liu | H05B 3/14 128/202.21 |
| 2014/0238423 | A1* | 8/2014 | Tucker | A24F 47/008 131/328 |
| 2015/0136124 | A1 | 5/2015 | Aronie et al. | |
| 2015/0163859 | A1 | 6/2015 | Schneider et al. | |
| 2015/0245659 | A1* | 9/2015 | DePiano | B21D 53/06 392/397 |
| 2015/0335071 | A1* | 11/2015 | Brinkley | A61M 15/06 131/328 |
| 2017/0188626 | A1* | 7/2017 | Davis | A24F 47/008 |

FOREIGN PATENT DOCUMENTS

| | | | |
|---|---|---|---|
| CN | 103987142 | A | 8/2014 |
| CN | 203789147 | U | 8/2014 |
| CN | 104287098 | A | 1/2015 |
| CN | 204146334 | U | 2/2015 |
| CN | 104540246 | A | 4/2015 |
| CN | 104544568 | A | 4/2015 |
| EP | 2724630 | A1 | 4/2014 |
| EP | 2801273 | A2 | 11/2014 |
| WO | 2014150979 | A2 | 9/2014 |
| WO | 2014160055 | A1 | 10/2014 |

* cited by examiner

ELECTRONIC SMOKING DEVICE AND ATOMIZER

FIELD OF INVENTION

The present invention relates generally to atomizers and cartomizers for, as well as to electronic smoking devices, in particular to electronic cigarettes.

BACKGROUND OF THE INVENTION

An electronic smoking device, such as an electronic cigarette, typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic smoking devices, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other electronic smoking devices, a switch is used to power up the electronic smoking device to generate a puff of vapor.

Energy that may be provided by the electric power source, in particular a single use or rechargeable battery, is limited. Furthermore, heat produced by the atomizer may affect other components of the electronic smoking device.

SUMMARY OF THE INVENTION

In accordance with one aspect of the invention there is provided an atomizer for an electronic smoking device with a heating wire. The heating wire is at least section-wise formed as a heating coil comprising a plurality of windings. The heating wire comprises a first section and a second section, wherein the electrical resistance per length unit of the first section differs from the electrical resistance per length unit of the second section. The heating coil has a first winding, a last winding and at least one inner winding between the first winding and the last winding. The at least one inner winding comprises the first section, the first winding comprises the second section, and the last winding comprises a third section. The electrical resistance per length unit of the third section corresponds to the electrical resistance per length unit of the second section In accordance with another aspect of the invention, there is provided a cartomizer for an electronic smoking device with an atomizer. The atomizer is an atomizer according to the invention. In accordance with yet another aspect of the invention, there is provided an electronic smoking device with an atomizer. The atomizer is an atomizer according to the invention.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
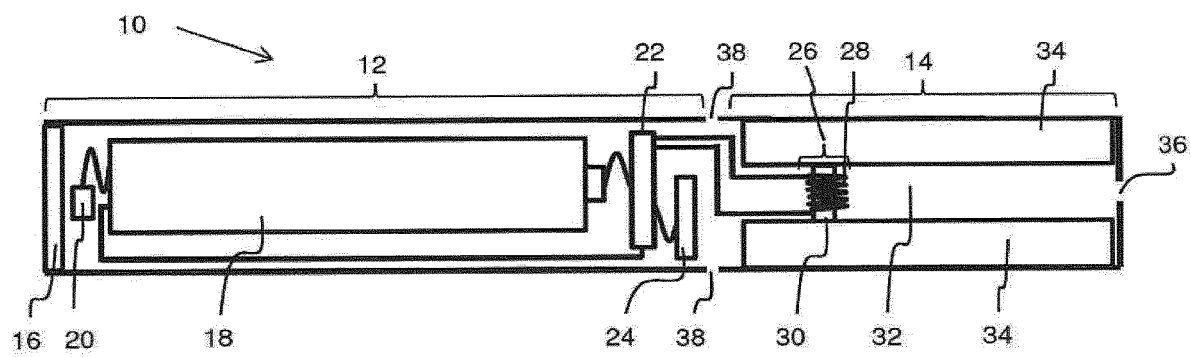
FIG. 1 is a schematic cross-sectional illustration of an exemplary embodiment of an electronic smoking device.

As is shown in FIG. 1, an electronic smoking device 10, which may be an e-cigarette, typically has a housing comprising a cylindrical hollow tube having an end cap 16. The cylindrical hollow tube may be a single piece or a multiple piece tube. In FIG. 1, the cylindrical hollow tube is shown as a two piece structure having a battery portion 12 and an atomizer/liquid reservoir portion 14. Together, the battery portion 12 and the atomizer/liquid reservoir portion 14 form a cylindrical tube which is approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid reservoir portion 14 are typically made of steel or hardwearing plastic and act together with the end cap 16 to provide a housing to contain the components of the electronic smoking device 10. The battery portion 12 and an atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap. The end cap can be made of metal or other materials that do not allow light to pass.

A battery 18, a light emitting diode (LED) 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the electronic smoking device 10. The airflow sensor 24 can be any suitable sensor for detecting changes in airflow or air pressure such a microphone switch including a deformable membrane which is caused to move by variations in air pressure. Alternatively, the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The heating coil 28 may be positioned anywhere in the atomizer 26 and may be transverse or parallel to the liquid reservoir 34. The wick 30 and heating coil 28 do not completely block the central passage 32. Rather, an air gap is provided on either side of the heating coil 28 enabling air to flow past the heating coil 28 and the wick 30. The heating coil 28 comprises a heating wire that is at least section-wise formed as the heating coil 28 and with a plurality of windings. The heating wire comprises a first section and a second section, wherein the electrical resistance per length unit of the first section differs from the electrical resistance per length unit of the second section. The length unit is measured along the heating wire. For the sake of clarity, however, the first and second sections are not shown in FIG. 1 in a distinguishable manner.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include a sponge-like material, e.g. wadding, soaked in liquid, wherein the sponge-like material encircles the central passage 32 with the ends of the wick 30 abutting or extending into the wadding. In other embodiments the liquid reservoir 34 may comprise a toroidal cavity arranged to be filled with liquid and/or the sponge-like material and with the ends of the wick 30 extending into the toroidal cavity.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or maybe formed in an end cap.

An air inlet may be provided in the end cap 16, at the edge of the inlet next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

In use, a user sucks on the electronic smoking device 10. This causes air to be drawn into the electronic smoking device 10 via one or more air inlets, such as the air inlets 38, and to be drawn through the central passage 32 towards the air inhalation port 36. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized creating an aerosol (which may comprise gaseous and liquid components) within the central passage 32. As the user continues to suck on the electronic smoking device 10, this aerosol is drawn through the central passage 32 and inhaled by the user. At the same time, the control electronics 22 also activate the LED 20 causing the LED 20 to light up, which is visible via the translucent end cap 16, mimicking the appearance of a glowing ember at the end of a conventional cigarette. As liquid present in the wick 30 is converted into an aerosol, more liquid is drawn into the wick 30 from the liquid reservoir 34 by capillary action and, thus, is available to be converted into an aerosol through subsequent activation of the heating coil 28.

Some electronic smoking devices are intended to be disposable and the electric power in the battery 18 is intended to be sufficient to vaporize the liquid contained within the liquid reservoir 34; after the battery has been spent, the electronic smoking device 10 is thrown away. In other embodiments, the battery 18 is rechargeable and the liquid reservoir 34 is refillable. In the cases where the liquid reservoir 34 is a toroidal cavity, this may be achieved by refilling the liquid reservoir 34 via a refill port. In other embodiments, the atomizer/liquid reservoir portion 14 of the electronic smoking device 10 is detachable from the battery portion 12 and a replacement atomizer/liquid reservoir portion 14 can be fitted with a replacement liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer or a clearomizer.

The replacement liquid reservoir 34 may be in the form of a cartridge having a central passage 32, through which a user inhales aerosol. In other embodiments, aerosol may flow around the exterior of the cartridge 32 to an air inhalation port 36.

Of course, in addition to the above description of the structure and function of the electronic smoking device 10, variations also exist. For example, the LED 20 may be omitted. The airflow sensor 24 may be placed adjacent the end cap 16 rather than in the middle of the electronic smoking device. The airflow sensor 24 may be replaced with a switch, which enables a user to activate the electronic smoking device manually rather than in response to the detection of a change in airflow or air pressure.

Different types of atomizers may be used. Thus, for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body.

Figure 2:
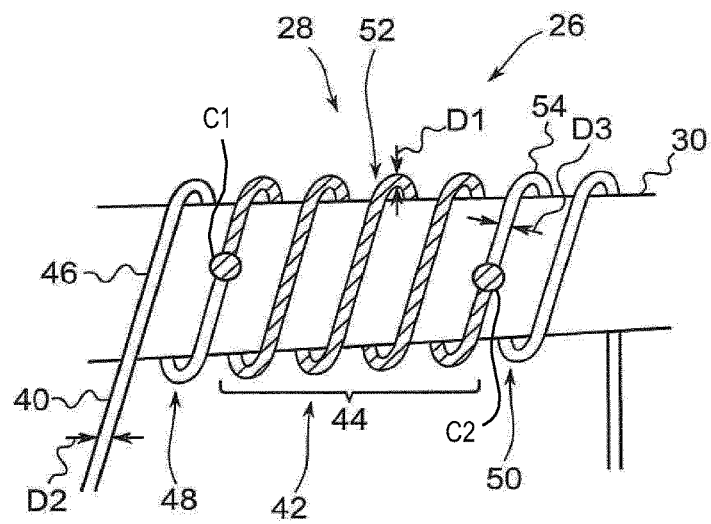
FIG. 2 shows an exemplary embodiment of an atomizer in a schematic side view.

FIG. 2 shows the atomizer 26 of FIG. 1 schematically in an enlarged side view.

The heating coil 28 is formed of a heating wire 40, that is wound around the wick 30, such that the heating coil 28 comprises a plurality of windings and for example seven windings 42.

The heating wire 40 comprises a first section 44 and a second section 46, wherein the electrical resistance per length unit of the first section 44 differs from the electrical resistance per length unit of the second section 46. By providing the heating wire 40 with the first and the second sections 44, 46 with different electrical resistances per length unit, the part of the atomizer 26, which provides heat for atomizing the liquid, can be limited. Hence, elements or areas of the electronic smoking device 10, which shall not be heated, can be protected from the heat caused by the heating wire 40 as these elements are at least not directly heated. Furthermore, by focusing the heat to a pre-determined area, for example the wick 30, heating energy provided by the battery 18 can be used more efficiently.

For example, the electrical resistance per length unit of the first section 44 is higher than the electrical resistance per length unit of the second section 46. In particular, the first section 44 can be used for transforming electrical energy provided by the battery 18 into heat energy. In particular, essentially only the first section 44 and not the second section 46 generates heat energy for atomizing or vaporizing the liquid.

In order to provide that essentially only the first section 44 generates heat for atomizing the liquid, the electrical resistance per length unit of the second section 46 is for example negligible compared to the electrical resistance per length unit of the first section such that over 90%, over 95% or even over 99% of the heat generated by the heating coil is generated by the first section. For example, the negligible electrical resistance per length unit of the first section 44 can essentially correspond to the electrical resistance per length unit of the second section 46 multiplied with a factor of at least 10 or between 10 and 1000, for example 100, 250, 500 or 750 or even more.

According to an embodiment, the first section 44 and the second section 46 are made of the same material, wherein the diameter $D_1$ of the heating wire 40 of the first section 44 is less than the diameter $D_2$ of the heating wire 40 of the second section 46. Due to the different diameters, the electrical resistances per length unit of the sections 44, 46 differ from each other.

Alternatively or additionally, the first section 44 is made of a first material and the second section 46 is made of a second material. The first material has an electrical conductivity that differs from the electrical conductivity of the second material. In particular, the electrical conductivity of the first material is less than the electrical conductivity of the second material. The electrical conductivity preferably has the unit siemens or Mho. For example, the first material is nichrome, whereas the second material may be copper or aluminum or an alloy with a lower resistance per length unit or resistivity. Hence, the second material may have an electrical conductivity that is higher that the electrical conductivity of the first material. The sections 44, 46 may be interconnected by a connecting area $C_1$, which may be formed by soldering or welding or the like.

In general, the heating coil 28 has a first winding 48, a last winding 50, and at least one inner winding 52 between the first winding 48 and the last winding 50, wherein the at least one inner winding 52 comprises the first section 44, the first winding 48 comprises the second section 46 and the last winding 50 comprises a third section 54, whose electrical resistance per length unit corresponds to the electrical resistance per length unit of the second section 46. For example, the second section 46 and the third section 54 are formed of the same material, in particular of the second material. Alternatively or additionally, the diameter $D_2$ of the heating wire 40 of the second section 46 corresponds or is equal to a diameter $D_3$ of the heating wire 40 of the third section 54. The first section 44 and the third section 54 may be interconnected by a connecting area $C_2$, which may be formed by soldering or welding or the like.

The heating coil 28 of the exemplary embodiment of FIG. 2 comprises a plurality of inner windings 52 that consist of the first section 44. Alternatively, the first and/or the third sections 44, 54 can comprise at least a section of one or more windings that directly follow or precede the first or the last winding 48, 50 in addition to the first or the last winding 48, 50.

The atomizer 26 of the exemplary embodiment of FIG. 2 is the atomizer 26 of the electronic smoking device 10 shown in FIG. 1. Alternatively, the atomizer 26 may be part of a cartomizer. In case a liquid reservoir of the cartomizer is transparent such that a liquid level in the liquid reservoir can be visually inspected, the cartomizer may also be designated as a clearomizer. Furthermore, the liquid reservoir of the clearomizer may not comprise any sponge-like material.

Figure 3:
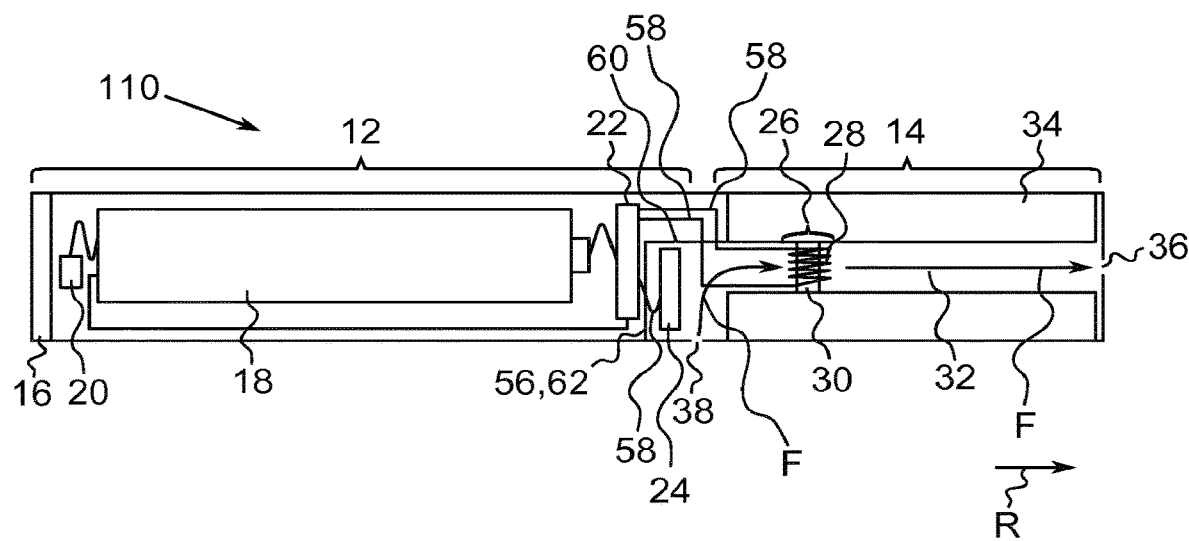
FIG. 3 shows another exemplary embodiment of the electronic smoking device with the atomizer of FIG. 2 in a schematic cross-sectional view.

FIG. 3 shows another exemplary embodiment of the electronic smoking device 10 of FIG. 1. For the sake of brevity, only the differences from the exemplary embodiment of FIG. 1 are described in the following.

The electronic smoking device 110 does not comprise two air inlets 38 that are provided opposite of each other, but only one of the two air inlets 38 shown in FIG. 1. Furthermore, the electronic smoking device 110 of the exemplary embodiment shown in FIG. 3 comprises an inner guidance housing 56, through which a gas flow path F extends from the air inlet 38 to the air inhalation port 36. Through the central passage 32, the flow path F extends along a longitudinal direction R of the electronic smoking device 110. The inner guidance housing 56 prevents that atomized liquid can stream from the atomizer 26 into the battery portion 12 and/or to the control electronics 22. The airflow sensor 24 is arranged within the inner guidance housing 56, such that air entering through the air inlet 38 flows along the flow path F and the airflow sensor 24. Hence, the flow path F extends along the airflow sensor 24. Connection wires 58 for connecting the atomizer 26 and/or the airflow sensor 24 with the control electronics 22 extend through at least one of the side walls 60, 62 of the inner guidance housing 56.

The side walls 60, 62 of the inner guidance housing 56 are arranged to have an L-shaped cross-section along a longitudinal direction R of the electronic smoking device 110, wherein the side walls 60, 62 are closed side walls without any openings.

Figure 4:
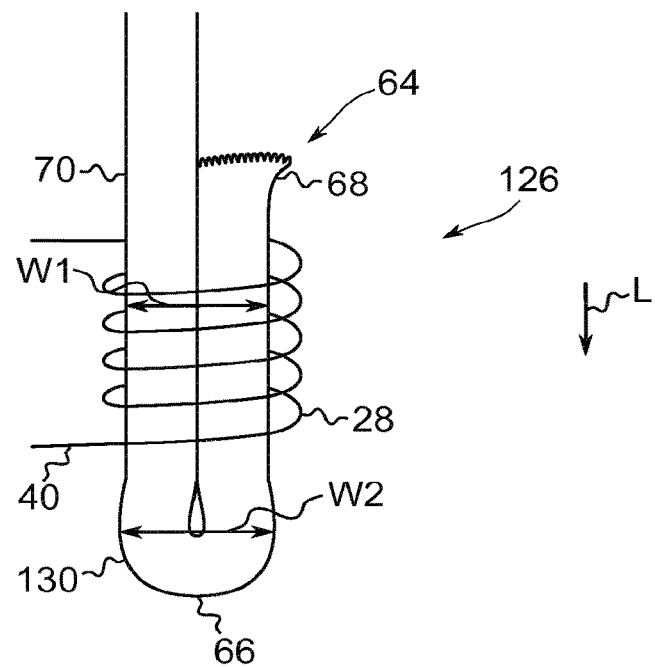
FIG. 4 shows another exemplary embodiment of the atomizer in a schematic cross-sectional view.

FIG. 4 shows another exemplary embodiment of the atomizer. For the sake of brevity, only the differences between the atomizer of the exemplary embodiment of FIG. 4 and the atomizer 26 of the exemplary embodiment of FIG. 2 are described in the following.

The atomizer 126 of the exemplary embodiment of FIG. 4 comprises the heating coil 28 of the atomizer 26 shown in FIG. 2. However, the wick 130 of the exemplary embodiment of FIG. 4 differs from the wick 30 of the exemplary embodiment of the previous figures. In particular, the wick 130 is formed with a free end 64 that is folded back onto another section of the wick 130. In particular in case the wick 130 is made of fibrous material, single fibers that may protrude from the free end 64 do not affect the operation of the electronic smoking device 10 due to the folded configuration of the wick 130.

A free end 66 of the atomizer 126 is formed by a curved or bent section of the wick 130. The free end 66 interconnects a first section 68 and a second section 70 of the wick 130. The first section 68 extends between the free end 66 of the atomizer 126 and the free end 64 of the wick 130. The first section 68 and the second section 70 extend parallel to and are in contact with each other. In case the first and second sections 68, 70 have the same length, the wick 130 is U-shaped, wherein the legs of the U are formed by the first and section sections 68, 70. According to the exemplary embodiment shown in FIG. 4, however, the first and second sections 68, 70 have different lengths. In particular, the length of the first section 68 between the free ends 64, 66 is less than the length of the second section 70 that is to be measured away from the free end 66. Thus, the wick 130 shown in FIG. 4 is essentially J-shaped.

The first and second sections 68, 70 contact each other, as shown in FIG. 4. In order to keep the first and second sections 68, 70 of the wick 130 in close contact, the heating wire 40 is tightly wound around the first and second sections 68, 70 and presses the first and second sections 68, 70 against each other. The free end 66 of the atomizer 126 formed by the curved portion of the wick 130 protrudes from the heating coil 28 in a longitudinal direction L of the heating coil 28.

In case the heating wire 40 presses the first and second sections 68, 70 against each other perpendicular to the longitudinal direction L, a combined width $W_1$ of the first and the second sections 68, 70 with the heating coil 28 is less than a maximum width $W_2$ of the curved section of the wick 130 that forms the free end 66 of the atomizer 126. Preferably, the widths $W_1$, $W_2$ are to be measured perpendicularly to the longitudinal direction L.

The embodiment of the wick 130 is advantageous on its own and independent of the embodiment of the heating coil 28 and its heating wire 40.

Figure 5:
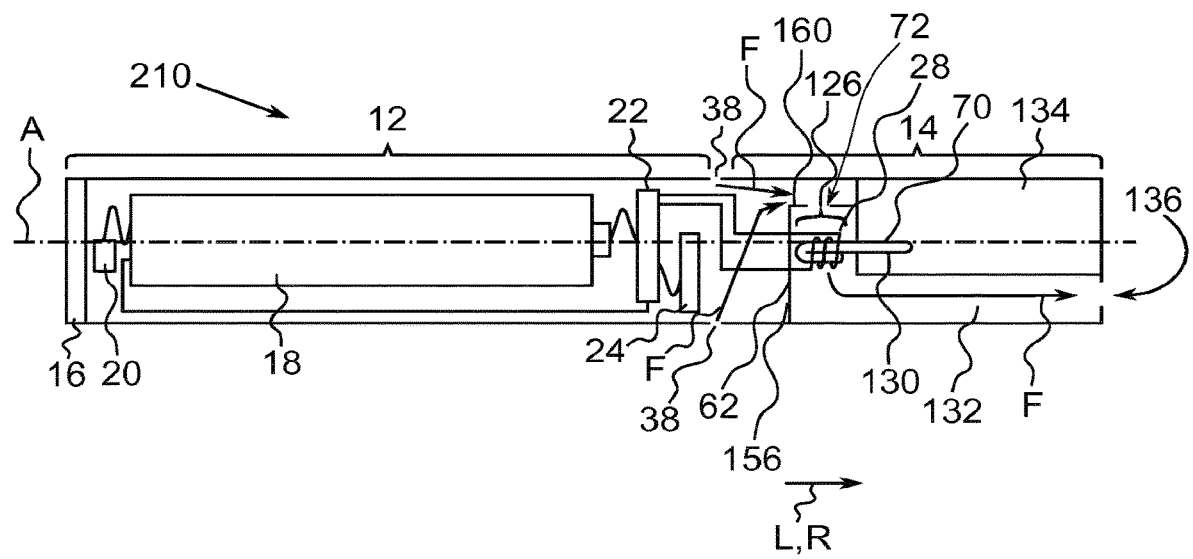
FIG. 5 shows another exemplary embodiment of the electronic smoking device comprising the atomizer of FIG. 4 in a schematic cross-sectional view.

FIG. 5 shows another exemplary embodiment of the electronic smoking device with the atomizer 126 of the exemplary embodiment of FIG. 4. For the sake of brevity, only the differences between the exemplary embodiment of FIG. 5 and the electronic smoking devices of the exemplary embodiments of FIGS. 1 and 3 are described in the following.

The atomizer 126 is an axial atomizer, as the longitudinal direction L of the heating coil 28 extends in parallel to a longitudinal or center axis A of the electronic smoking device 210 of the electronic smoking device 210, which extends in parallel to the longitudinal direction R. In particular, the axis A may coincide with a central axis of the heating coil 28 or may be arranged at a distance to the central axis of the heating coil.

The electronic smoking device 210 comprises the two opposite air inlets 38. Alternatively, one of the air inlets 38 can be omitted.

The electronic smoking device 210 comprises another exemplary embodiment of the inner guidance housing 156 with the side wall 62 and a side wall 160. The side wall 160 extends essentially parallel to the axis A and is formed with an opening 72. The flow path F extends from the one air inlet 38 or from all air inlets 38 through the opening 72 to the atomizer 126 along the atomizer 126, where it picks up atomized liquids and along a liquid reservoir 134 towards the air inhalation port 136. Within the guidance housing 156, the flow path F extends essentially perpendicular to the longitudinal direction L of the heating coil 28 and to the wick 130, in order to efficiently pick up atomized or vaporized liquid.

Due to the inner guidance housing 156, the axial atomizer 126 can be used with a conventional electronic smoking device, such that available electronic smoking devices can be readily adapted to the axial atomizer 126.

The first and the second sections 68, 70 of the wick 130 can extend into the liquid reservoir 134 parallel to the axis A. Alternatively, as shown in FIG. 5, only the second section 70 of the wick 130 extends into the liquid reservoir 134. In case the central or winding axis of the heating coil 28 is arranged at a distance to the axis A of the electronic smoking device 210, the electronic smoking device 210 can be formed with the liquid reservoir 134. As shown in FIG. 5, in case the central or winding axis of the heating coil 28 is close to or coincides with the axis A of the electronic smoking device 210, the liquid reservoir 134 needs to be adapted such that it extends from a side wall of the liquid reservoir portion 14 towards and beyond the axis A.

In case the liquid reservoir 134 extends towards and beyond the axis A, the central passage 32 can be shifted towards the opposite side of the liquid reservoir portion 14 and is designated with the reference numeral 132. The passage 132 can extend along and contact a side wall of the liquid reservoir portion 14, that is arranged opposite of another side of the liquid reservoir portion 14, which is contacted by the liquid reservoir 134.

In order to be able to store a maximum amount of liquid in the liquid reservoir 134, the liquid reservoir 134 of the exemplary embodiment of FIG. 5 extends until an end of the electronic smoking device 210 that is opposite to the end cap 16. In order to be able to let the flow path F exit the electronic smoking device 210 through the air inhalation port 136, the air inhalation port 136 is arranged at a distance from the axis A and in particular between the axis A and the side of the liquid reservoir portion 14 that is opposite to the side that contacts the liquid reservoir 134.

The provision of the axial atomizer 126 with or without the inner guidance housing 156 is advantageous independent of the provision of the heating coil 28 with the heating wire 40 having the first and second sections 44, 46.

Alternatively, the wick is U-shaped and/or may be installed as the wick 30 with its lateral ends contacting the liquid reservoir 34 as shown in FIGS. 1 and 3.

Figure 6:
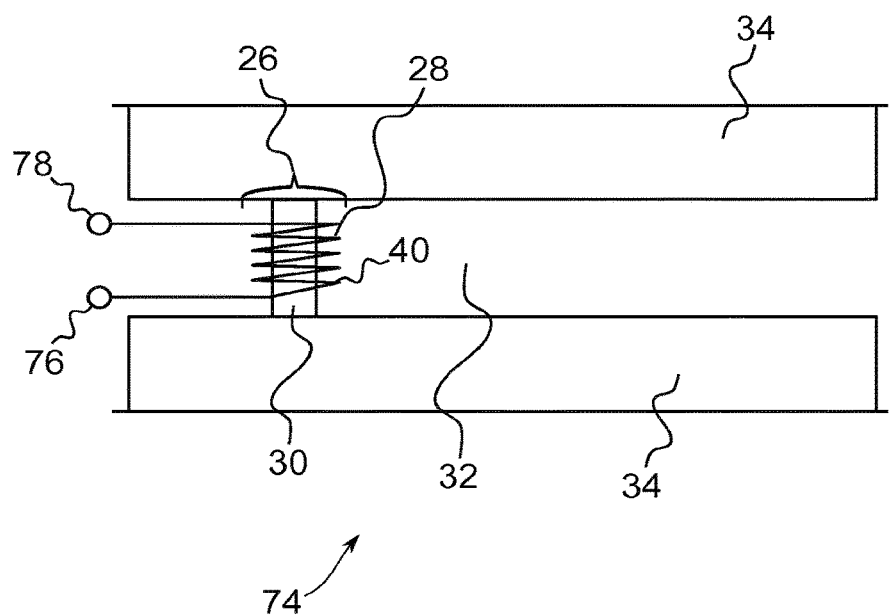
FIG. 6 schematically shows an exemplary embodiment of a cartomizer.

FIG. 6 shows an exemplary embodiment of a cartomizer with the atomizer 26 of the previous exemplary embodiment of FIG. 2 and the liquid reservoir 34 in a schematic cross-sectional view.

The cartomizer 74 is shown with contact elements 76, 78 for electrically connecting the heating coil 28 to the power supply of an electronic smoking device that is adapted to be connected to and to be used with the cartomizer 74. The contact elements 76, 78 are shown mounted at free ends of the heating wire 40, for the sake of simplicity. Yet, the contact elements 76, 78 may be affixed in or at the cartomizer 74, for example at the liquid reservoir 34.

The cartomizer 74 may be inserted into the atomizer/liquid reservoir portion 14 of the electronic smoking device. Optionally, the cartomizer 74 may be the atomizer/liquid reservoir portion 14 once mounted to the electronic smoking device Essentially, the structure of the cartomizer 74 corresponds to the structure of the atomizer/liquid reservoir portion 14 of the exemplary embodiment of FIG. 1. Alternatively, the structure of the cartomizer 74 may correspond to the structure of the atomizer/liquid reservoir portion 14 of the exemplary embodiments of FIG. 1 or 2.

Alternatively, the wick shown in FIG. 6 is J- or U-shaped.

Figure 7:
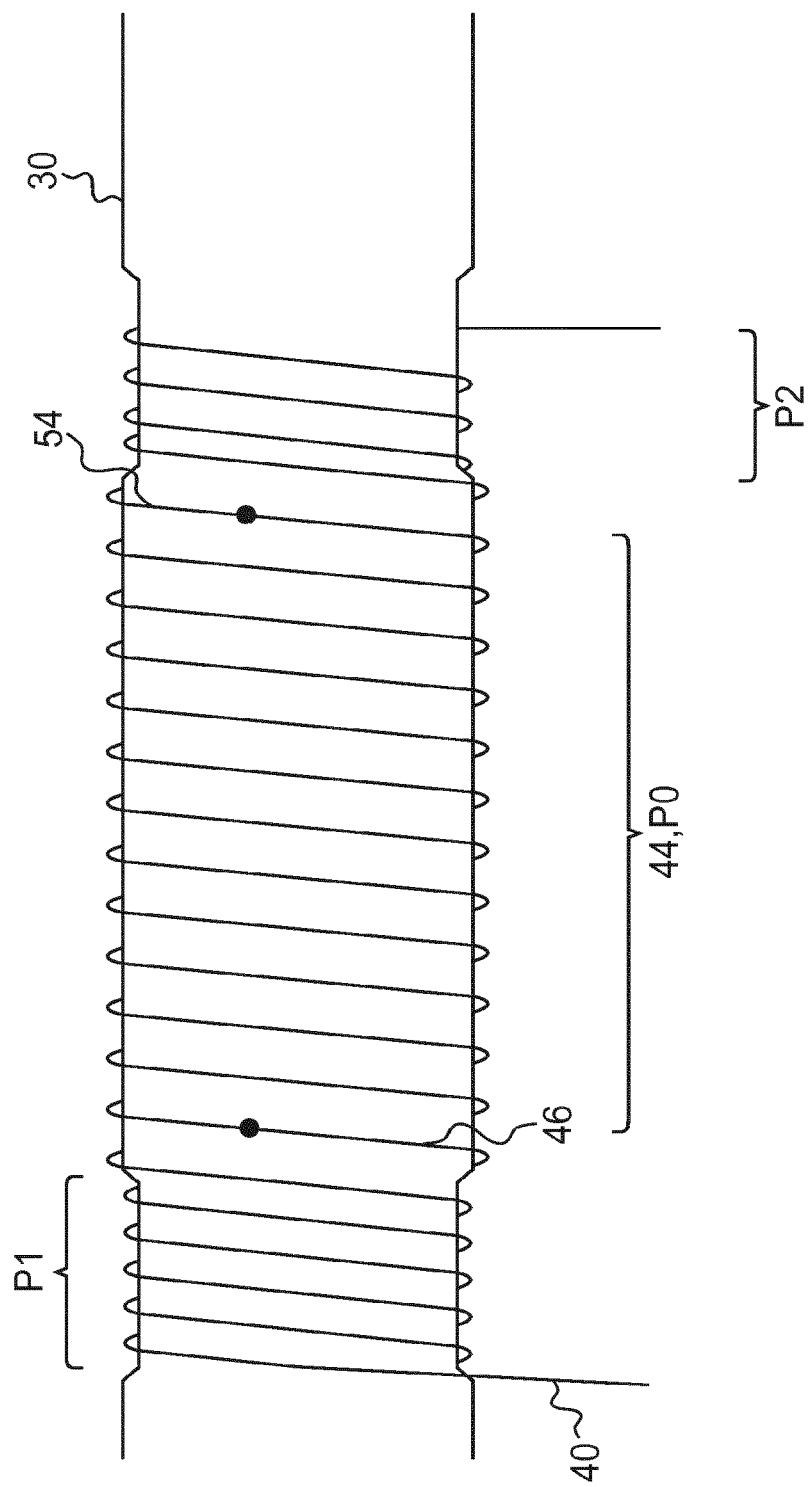
FIG. 7 shows an exemplary embodiment of a wick.

FIG. 7 shows the wick 30 of the exemplary embodiments of FIGS. 1 to 3 and 6 in a side view.

The wick 30 is shown as a single wick. In the alternative, the wick may be the J-shaped wick of the exemplary embodiment of FIG. 4, or a U-shaped wick with two sections 68, 70 with the same length being folded onto each other.

The heating wire 40 comprises the first section 44, the second section 46 and the third section 54. The second section 46 and the third section 54 are wound around the wick 30 tighter than the first section 44. In particular, the second section 46 and the third section 54 are wound tight around the wick 30 in order to compress the wick 30, thereby affixing the heating wire 40 to the wick 30, e.g. by a force fit. Due to the tight winding, the wick 30 may be compressed more by the second section 46 and by the third section 54 than by the first section 44. Hence, the wick 30 may comprise at least one compressed section P1 and optionally two compressed sections P2 and a less or even not compressed section P0 between the compressed sections P1, P2.

The first section 44 of the heating wire 40 is at least sectionwise of even completely coiled around the less or not compressed section P0 of the wick 30. The second section 46 and/or the third section 54 are each coiled around one of the compressed sections P1, P2. The second section 46 and/or the third section 54 may form at least one winding or a plurality of windings that are coiled tighter around the wick 30 than the first section 44 of the heating wire 40. The second section 46 may form at least one winding or a plurality of first windings 48 and the third section 54 may form at least one winding or a plurality of last windings 50. For example, between two and six and e.g. three, four or five windings of the first and/or the second section 44, 46 compress the wick 30 more than the first section 44 of the heating wire 40.

Alternatively, the wick shown in FIG. 7 is J- or U-shaped.

It will also be appreciated that although in some embodiments a puff detector (utilizing an airflow sensor) for detecting a user puffing on a device could be provided and the puff detector could be arranged to initiate the activation of an atomizer when a user puffed on the device, in some embodiments the puff detector could be replaced by a push button and a user could cause an atomizer to activate by pressing on the button. In other embodiments, other means for activating the device could be provided.

In summary, according to one aspect, the atomizer has a heating wire that is at least section-wise formed as a heating coil comprising a plurality of windings. The heating wire comprises a first section and a second section. The electrical resistance per length unit of the first section differs from the electrical resistance per length unit of the second section, such that heat generated by the heating wire can be generated at a pre-determined position and less or even no heat is generated by the heating wire at a position, where no heat is required for the operation of the atomizer and in particular for atomizing or vaporizing liquid. The length unit is measured along the heating wire.

According to another aspect, a cartomizer for an electronic smoking device may be provided, wherein the cartomizer comprises an atomizer and a liquid reservoir. The atomizer of such a cartomizer may be an atomizer as explained above and in the following.

In case the liquid reservoir of the cartomizer is transparent, the cartomizer may be designated as a clearomizer.

Within the liquid reservoir, only liquid to be atomized or a sponge-like material containing the liquid to be atomized may be present.

According to yet another aspect, an electronic smoking device may be provided, wherein the electronic smoking device comprises an atomizer and a liquid reservoir. The atomizer of such an electronic smoking device may be the atomizer described above and in the following.

The electrical resistance per length unit of the first section may be higher than the electrical resistance per length unit of the second section. Hence, an advantage may be that essentially only the first section generates heat required for the operation of the atomizer and in particular to atomize or to vaporize liquid, whereas the second section generates less or even a negligible quantity of heat when the atomizer is operated and heating current is led through the heating wire.

The electrical resistance per length unit of the second section may be negligible compared to the electrical resistance per length unit of the first section such that over 90%, over 95% or even over 99% of the heat generated by the heating coil is generated by the first section. For example, the negligible electrical resistance per length unit of the first section may correspond to the electrical resistance per length unit of the second section multiplied by a factor of at least 10 or between 10 and 1000 and for instance 100, 250, 500 or 750 or even more. A possible advantage of such a resistance per length unit ratio may be that essentially only the first section contributes to the atomizing or vaporizing of the liquid, and the second section does not generate any or, compared to the first section, very little heat. Hence, electrical energy used to produce heating energy with the atomizer for vaporizing liquid is efficiently used essentially only in the first section.

The diameter of the heating wire of the first section may be less than the diameter of the heating wire of the second section. An advantage of such a heating wire may be that it can be easily produced from a standard wire, whose first section is thinned compared to the second section, wherein the first section and the second section may be made of the same material.

Alternatively or additionally, the first section may be made of a first material and the second section may be made of a second material. The first material may have an electrical conductivity that differs from the electrical conductivity of the second material. Thinning a wire, namely, may have the disadvantage that the thinned first section may be mechanically weak and may deteriorate faster than an unthinned section of the heating wire during operation of the atomizer. Furthermore, another possible advantage may be that the electrical conductivities of the first and the second sections can be better controlled and pre-selected when using different materials compared to using different diameters for generating the different electrical conductivities. Finally, another possible advantage may be that the ratio between the electrical conductivities may be higher in case different materials and optionally different diameters are used. The electrical conductivity preferably has the unit siemens or Mho. For example, the first material is nichrome, whereas the second material may be copper or aluminum or an alloy with a lower resistance per length unit.

The first section and the second section may be formed continuously or may be interconnected by a material fit, e.g. by welding or soldering. Thus, sections with different diameters and/or different materials can be firmly connected to each other without affecting electrical conductivity at connecting areas.

The heating coil may have a first winding, a last winding, and at least one inner winding between the first winding and the last winding. The at least one inner winding may comprise or even consist of the first section. The first winding may comprise the second section. In particular, the second section may at least section-wise form the first winding and optionally at least a section of at least one winding following the first winding. The last winding comprises a third section, whose electrical resistance per length unit corresponds to the electrical resistance per length unit of the second section. Again, at least a section of the third section may form the last winding and optionally at least a section of at least one winding preceding the last winding. An advantage may be that essentially only an inner section of the heating coil is used for generating atomizing or vaporizing heat, whereas outer parts of the coil generate no or less heat. Hence, lead wires that interconnect the heating coil with a power supper and in particular with the control electronics of an electronic smoking device may not unduly heat up and prevent that an undue amount of heat is transmitted to the electronics or other parts of the electronic smoking device.

The first winding and one of the lead wires may be formed of the second section. The last winding and another one of the lead wires may be formed of the third section. In particular, the electrical, material and/or geometrical properties, such as the diameter, of the third winding may correspond to the electrical, material and/or geometrical properties, such as the diameter, of the second winding.

The heating coil may comprise a plurality of inner windings that consist of the first section. Hence, an advantage of such a heating coil may be that the heating coil emits heat over a larger area, this area essentially corresponding to a lateral surface of a cylinder that can be placed inside of the heating coil, the length of the cylinder being limited by the plurality of inner windings, such that isolated heat spots are prevented and a sufficient amount of liquid can be atomized or vaporized.

The second section and/or the third section of the heating wire may be wound around the wick tighter than the first section. In particular, the second section and/or the third section may be wound tight around the wick in order to compress the wick, thereby affixing the heating wire to the wick, e.g. by a force fit. Due to the tight winding, the wick may be more compressed by the second section and/or the third section than by the first section. Hence, the wick may comprise compressed sections and a less or even not compressed section between the compressed sections. The first section of the heating wire is at least sectionwise of even completely coiled around the less or not compressed section of the wick and the second section and/or the third section are each at least sectionwise coiled around one of the compressed sections. The second section and/or the third section may form at least one winding or a plurality of windings that are coiled tighter around the wick than the windings of the first section of the heating wire. For example, between two and six and e.g. three, four or five windings of the first and/or of the second section compress the wick more than the first section of the heating wire. The second section and/or the third section may extend onto the less or not compressed section of the wick for up to one or more windings.

An advantage of this embodiment may be that the heating wire is securely fixed to the wick without the need for separate fixing elements, thereby reducing structural complexity and facilitating production of the atomizer.

Instead of using electronic smoking device with liquids comprising nicotine and/or flavored materials, the electronic smoking device may be used to apply medical materials to be inhaled. Such inhalants can be atomized or vaporized and inhaled like the liquid and may even be provided in the liquid reservoir. In case the electronic smoking device is deemed to be used to providing vapour containing medicine to be inhaled, and e.g. in case the medicine to be inhaled is present in the liquid reservoir, the medicine to be inhaled may be designated as medical device and/or inhaler. An advantage of such a device with the heating wire that comprises the first and the second section may be that medical materials are prevented from being overheated due to the concentrated generation of heat.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10, 110, 210 electronic smoking device
12 battery portion
14 atomizer/liquid reservoir portion
16 end cap
18 battery
20 light emitting diode (LED)
22 control electronics
24 airflow sensor
26, 126 atomizer
28 heating coil
30, 130 wick
32, 132 central passage
34, 134 liquid reservoir
36, 136 air inhalation port
38 air inlets
40 heating wire
42 winding
44 first section
46 second section
48 first winding
50 last winding
52 inner winding
54 third section
56, 156 inner guidance housing
58 connection wires
60, 62, 160 side walls
64 free end of 130
66 free end of 126
68 first section of 130
70 second section of 130
72 opening in 160
74 cartomizer
76, 78 contact element
A axis of 210
$C_1$, $C_2$ connecting area
$D_1$ diameter of 44
$D_2$ diameter of 46
$D_3$ diameter of 54
F flow path
L longitudinal direction of 28
R longitudinal direction of 110
$W_1$ width of 68, 70
$W_2$ width of 66

The invention claimed is:

1. An atomizer for an electronic smoking device comprising:
a heating wire that is at least section-wise formed as a heating coil comprising a plurality of windings, the heating wire comprising a first section and a second section, the heating coil has a first winding, a last winding and at least one inner winding between the first winding and the last winding, wherein the at least one inner winding comprises the first section, the first winding comprises the second section, and the last winding comprises a third section, wherein the electrical resistance per length unit of the third section corresponds to the electrical resistance per length unit of the second section, wherein the electrical resistance per length unit of the first section differs from the electrical resistance per length unit of the second section to increase the electrical resistance per unit length of the first section to generate heat for vaporizing liquid.

2. The atomizer of claim 1, wherein the electrical resistance per length unit of the first section is higher than the electrical resistance per length unit of the second section.

3. The atomizer of claim 1, wherein the electrical resistance per length unit of the first section corresponds to the electrical resistance per length unit of the second section multiplied by a factor of at least 10.

4. The atomizer of claim 1, wherein the diameter of the heating wire of the first section is less than the diameter of the heating wire of the second section.

5. The atomizer of claim 1, wherein the first section is made of a first material, and the second section is made of a second material, wherein the first material has an electrical conductivity that differs from the electrical conductivity of the second material.

6. The atomizer of claim 1, wherein the first section and the second section are formed continuously or are interconnected by a material fit.

7. The atomizer of claim 1, wherein the heating coil comprises a plurality of inner windings that consist of the first section.

8. The atomizer of claim 1, wherein the atomizer comprises a wick that is formed with a free end that is folded back onto another section of the wick.

9. A cartomizer for an electronic smoking device the cartomizer comprising:
a liquid reservoir;
a wick configured to draw liquid from the liquid reservoir; and
an atomizer including a heating wire that is at least section-wise formed as a heating coil comprising a plurality of windings wrapped around the wick, the heating wire comprising a first section and a second section, the heating coil has a first winding, a last winding and at least one inner winding between the first winding and the last winding, wherein the at least one inner winding comprises the first section, the first winding comprises the second section, and the last winding comprises a third section, wherein the electrical resistance per length unit of the third section corresponds to the electrical resistance per length unit of the second section, wherein the electrical resistance per length unit of the first section differs from the electrical resistance per length unit of the second section to increase the electrical resistance per unit length of the first section to generate heat for vaporizing liquid.

10. The cartomizer of claim 9, wherein the electrical resistance per length unit of the first section is higher than the electrical resistance per length unit of the second section.

11. The cartomizer of claim 9, wherein the electrical resistance per length unit of the first section corresponds to the electrical resistance per length unit of the second section multiplied by a factor of at least 10.

12. The cartomizer of claim 9, wherein the diameter of the heating wire of the first section is less than the diameter of the heating wire of the second section.

13. The cartomizer of claim 9, wherein the first section is made of a first material and the second section is made of a second material, wherein the first material has an electrical conductivity that differs from the electrical conductivity of the second material.

14. The cartomizer of claim 9, wherein the first section and the second section are formed continuously or are interconnected by a material fit.

15. An electronic smoking device including an atomizer comprising:
a battery portion, including a battery;
an atomizer/liquid reservoir portion configured for attaching to the battery portion, the atomizer/liquid reservoir portion including a liquid reservoir;
a wick configured to draw liquid from the liquid reservoir; and
the atomizer including a heating wire that is at least section-wise formed as a heating coil comprising a plurality of windings wrapped around the wick, the heating wire comprising a first section and a second section, the heating coil has a first winding, a last winding and at least one inner winding between the first winding and the last winding, wherein the at least one inner winding comprises the first section, the first winding comprises the second section, and the last winding comprises a third section, wherein the electrical resistance per length unit of the third section corresponds to the electrical resistance per length unit of the second section, wherein the electrical resistance per length unit of the first section differs from the electrical resistance per length unit of the second section to increase the electrical resistance per unit length of the first section to generate heat for vaporizing liquid.

16. The electronic smoking device of claim 15, wherein the electrical resistance per length unit of the first section is higher than the electrical resistance per length unit of the second section.

17. The electronic smoking device of claim 15, wherein the electrical resistance per length unit of the first section corresponds to the electrical resistance per length unit of the second section multiplied by a factor of at least 10.

18. The electronic smoking device of claim 15, wherein the diameter of the heating wire of the first section is less than the diameter of the heating wire of the second section.

19. The electronic smoking device of claim 15, wherein the first section is made of a first material and the second section is made of a second material, wherein the first material has an electrical conductivity that differs from the electrical conductivity of the second material.

20. The electronic smoking device of claim 15, wherein the first section and the second section are formed continuously or are interconnected by a material fit.

* * * * *